(12) United States Patent
Romaine et al.

(10) Patent No.: US 6,964,866 B2
(45) Date of Patent: Nov. 15, 2005

(54) METHODS AND COMPOSITIONS FOR HIGHLY EFFICIENT TRANSFORMATION OF FILAMENTOUS FUNGI

(75) Inventors: C. Peter Romaine, State College, PA (US); Xi Chen, Durham, NC (US)

(73) Assignee: The Penn State Research Foundation, University Park, PA (US)

( * ) Notice: Subject to any disclaimer, the term of this patent is extended or adjusted under 35 U.S.C. 154(b) by 431 days.

(21) Appl. No.: 09/894,630

(22) Filed: Jun. 28, 2001

(65) Prior Publication Data

US 2002/0016982 A1 Feb. 7, 2002

Related U.S. Application Data

(60) Provisional application No. 60/214,630, filed on Jun. 28, 2000.

(51) Int. Cl.$^7$ .............................. C12N 1/14; C12N 1/16; C12N 1/18; C12N 15/74; C12N 15/82
(52) U.S. Cl. ................... 435/254.11; 435/243; 435/440; 435/471; 435/469; 536/23.1
(58) Field of Search ............................ 435/254.11, 243; 435/440, 471, 469; 536/23.1

(56) References Cited

U.S. PATENT DOCUMENTS 6,255,115 B1 * 7/2001 Beijersbergen et al. ..... 435/477

FOREIGN PATENT DOCUMENTS

| WO | WO 95/02691 | 1/1995 |
| WO | WO 98/45455 | 10/1998 |

OTHER PUBLICATIONS

Stachel, et al., Identification of the signal molecules produced by wounded plant cells that activate T–DNA transfer in *Agrobacterium tumefaciens*, Nature vol. 318: 624–629, 1985.*
Buchanin, et al. Biochemistry & Molecular Biology of Plants (2000) American Society of Plant Physiologists, Rockville Md 20855, pp. 1146–1147 and 1276–1277.*
Bundock, et al., "Trans–kingdom T–DNA transfer from *Agrobacterium tumefaciens* to *Saccharomyces cerevisiae*", The EMBO Journal, vol. 14(13):3206–3214 (1995).
Chen, et al., "A Fruiting Body Tissue Method for Efficient *Agrobacterium*–Mediated Transformation of *Agaricus bisporus*", Applied and Environmental Microbiology, 66(10):4510–4513 (Oct. 2000).

deGroot, et al., "*Agrobacterium tumefaciens*–mediated transformation of filamentous fungi", Nature Biotechnology, 16:839–842 (1998).
Gouka, et al., "Transformation of *Aspergillus awamori* by *Agrobacterium tumefaciens*–mediated homologous recombination", Nature Biotechnology, 17:598–601 (1999).
Mikosch, et al., "Transformation of the cultivated mushroom *Agaricus bisporus* (Lange) using T–DNA from *Agrobacterium tumefaciens*," Curr Genet 39:35–39 (2001).
vandeRhee et al., "Transformation of the cultivated mushroo, *Agaricus bisporus*, to hygromycin B resistance", Mol. Gen. Genet, 250:252–258 (1996).
Mikosch T S P et al. "*Agrobacterium Tumefaciens* Mediated Transformation of *Agaricus Bisporus*" Mushroom Science, vol. 15, 2000, pp. 173–179 XP001053247; Proceedings of the 15th International Congress on the Science and Cultivation of Edible Fungi; Maastricht, Netherlands; May 15–19, 2000, 2000 A. A. Balkema 3000 BR, Rotterdam, Netherlands.
De Groot Marcel J A et al; "*Agrobacterium Tumefaciens*-Mediated Transformation of Filamentous Fungi"; Nature Biotechnology, vol. 16, No. 9, 1998, pp. 839–842.
Challen M P et al; "Transformation Technologies for Mushrooms"; Mushroom Science, vol. 15, 2000, pp. 165–172, XP001053246; Proceedings of the 15th International Congress on the Science and Cultivation of Edible Fungi; maastricht, netherlands; May 15–19, 2000 2000 A. A. Balkema 3000 BR, Rotterdam, Netherlands.
Chen Xi et al. "a Fruiting bODY Tissue Method for Efficient *Agrobacterium*–Mediated Transformation of *Agaricus Bisporus*"; Applied and Environmental microbiology, vol. 66, No. 10, Oct. 2000, pp. 4510–4513, XP002188897.

* cited by examiner

*Primary Examiner*—Elizabeth F. McElwain
*Assistant Examiner*—Georgia Helmer
(74) *Attorney, Agent, or Firm*—McKees, Voorhees & Sease, P.L.C.

(57) ABSTRACT

Applicants have devised a highly effective, convenient, and expeditious genetic transformation system for filamentous fungi, such as *Agaricus bisporus*. The preferred method uses an *Agrobacterium*-mediated transformation protocol. The critical features of this protocol include co-cultivation of the bacterium with fruit body tissue instead of spores. In a preferred embodiment, even higher transformation efficiencies were observed with the use of a homologous promoter in the polynucleotide expression construct in order to drive gene expression.

14 Claims, 3 Drawing Sheets

(3 of 3 Drawing Sheet(s) Filed in Color)

SEQUENCE LISTING

<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: gpd 3' primer

<400> SEQUENCE: 1
gaagaagctt taagaggtcc gc                                          22

<210> SEQ ID NO 2
<211> LENGTH: 20
<212> TYPE: DNA
<213> ORGANISM: Artificial
<220> FEATURE:
<223> OTHER INFORMATION: 5' Primer for gpd

<400> SEQUENCE: 2
ggcgacctcg tattggaatc                                             20

METHODS AND COMPOSITIONS FOR HIGHLY EFFICIENT TRANSFORMATION OF FILAMENTOUS FUNGI

CROSS-REFERENCE TO RELATED APPLICATIONS

This application claims benefit under 35 U.S.C. § 119(e) of provisional application No. 60/214,630 filed Jun. 28, 2000.

GRANT REFERENCE

Work for this invention was funded in part by a grant from the United States Department of Agriculture, under the Hatch Act (PEN03568). The Government may have certain rights in this invention.

FIELD OF THE INVENTION

This invention relates generally to the field of molecular biology. More specifically, this invention relates to the characterization of novel methods for the highly effective transformation of fungi. The methods of the invention can be used to improve fungal species by recombinant technologies known to those of skill in the art, such as the manipulation for increased pathogen, pest, and pesticide resistance, and yield and quality, extended produce shelf life, improved culinary, nutritional, and medicinal value, and the like, as well as for commercial production of heterologous proteins.

BACKGROUND OF THE INVENTION

Fungi are microscopic, spore-bearing organisms that lack chlorophyll and therefore derive nourishment from dead or living organic matter. Introductory Mycology (eds.). Alexopoulos, C. J., Mims, C. W., and Blackwell, M. (1996). $4^{th}$ edition. Chapter 1. Because they share characteristics of both plants and animals, they are classified separately in the kingdom Fungi. Within this kingdom, there are the "filamentous fungi", so named because their vegetative bodies consist of small thread-like filaments referred to as "hyphae". Typically, the hyphae grow in a branching fashion, spreading over or within the substrate used as a source of nourishment, thereby forming a network of hyphae called "mycelium". Thus, the mycelium is the vegetative body of the fungus. In the life cycle of most filamentous fungi, the vegetative mycelium gives rise to either asexual or sexual spores. Asexual spores are referred to by a variety of names, but commonly used terms are "conidia", "condiospores", or simply "spores". The vegetative mycelium of the fungus may differentiate, with the appropriate biological and environmental cues, into a sexual reproductive spore-bearing structure. Some fungi produce sizable, fibrous ("fleshy"), spore-bearing reproductive structures variously called "mushrooms" "fruit bodies" "basidiocarps", "ascocarps", "conks", or "basidomes". The fruit bodies of some fungi are edible; being valued for their culinary, nutritional, or medicinal qualities, and, as such, are highly sought after or grown commercially.

The fruit body may be differentiated into specialized tissues such as the fleshy umbrella-shaped cap (pileus), stem (stipe), cup at the base of the stem (volva), and gills (lamallae) bearing the sexual spores. A thin tissue known as the veil (velium) may cover the underside of the cap. The veil ruptures as the fruit body approaches maturity, exposing the gills and permitting the discharge of the sexual spores into the environment. However, the fruit bodies of some fungi lack gills all together, and instead are composed of fleshy tissue perforated with small pores or locules bearing the sexual spores. Sexual spores produced by the fleshy reproductive structures of fungi are described by numerous terms, as for example, "ascospores", "basidiospores", or simply "spores".

Thus, the fruit body of fungi is functionally comparable to the reproductive structure of plants known as the flower, whereas both asexual and sexual spores are comparable to the seed of plants, being important in the dispersal and survival of the fungus in nature. Under suitable environmental conditions, the spore germinates to form another generation of vegetative hyphae and so completing the life cycle of the fungus.

Filamentous fungi have a vital role as one of the primary decomposers within their varied natural habitats. They also have a large impact on food production. Some fungi, such as mushrooms, are used as food, while others are plant pathogens that are responsible for devastating crop losses all over the world. Filamentous fungi are also important in industry and medicine as they secret a diverse array of enzymes (e.g. proteases, lipases) as well as primary (e.g. organic acids) and secondary metabolites (e.g. antibiotics penicillin and cephalosporin). The cultivated mushroom *Agaricus bisporus* is a significant crop, with a world-wide production in 1990 of 1.5 million tons. Filamentous fungi are also attractive as hosts for large-scale production of both homologous and heterologous proteins, because they have the capacity to secrete substantial amounts of proteins.

About 40% of the commercially available enzymes are derived from filamentous fungi. Lowe, Handbook of Applied Mycology. Fungal Biotechnology (eds.) Arora, D. K. Elander, R. P. & Mukerji, K. G. 681–708 (Marcel Dekker, New York; 1992). These enzymes are usually produced by species of the genera *Aspergillus* and *Trichoderma*. Because they secrete large amounts of protein into the medium, they can be grown in large-scale fermentation, and they are generally accepted as safe for the food industry.

General problems associated with the commercial cultivation of mushrooms (*A. bisporus*) include diseases caused by pathogens like *Verticillium fungicola* (dry bubble), *Trichoderma harzianum* biotypes 2 and 4 (green mold), *Pseudomonas tolaasii* (blotch), and dsRNA viruses (La France disease and patch disease), the major insect pest [sciarid fly (*Lycoriella mali*)], an extremely short shelf life of the product related to bacterial spoilage and rapid senescence, and browning (bruising) of the fruit body associated with the action of endogenous poly-phenoloxidases (PPO, like tyrosinase). To further improve product quality, conventional breeding programs for *A. bisporus* have been only moderately successful and may not be sufficient in the long term. This is because conventional breeding techniques for fungi are highly time consuming, and because the genetic variation in commercially available strains is limited, offering little advancement by selection (Horgen et al. "Homology between mitochondrial DNA of *Agaricus bisporus* and an internal portion of a linear mitochondrial plasmid of *Agaricus bitorquis*" Curr Genet. 1991 Jun.; 19(6):495–502.

In the case of *A. bisporus*, the main problem for effective breeding strategies is caused by the rather abnormal life-cycle involving the unusual simultaneous segregation of either parental nucleus into one basidiospore. After outgrowth of this basidiospore, heterokaryotic mycelium is formed containing nuclei and genetic characteristics that do not differ from those present in the parental mycelium. In addition, only little recombinational activity is observed during meiosis (Summerbell et al. Genetics, October 123(2) 1989 pp. 293–300).

For this reason, investigators all over the world have attempted to develop a transformation system for commercial mushrooms, such as *A. bisporus*, for the introduction of novel characteristics. For other fungi, as well as plants, animals, and bacteria, the application of gene transfer technology is quite common and has already resulted in commercial application. However, the absence of an efficient, reproducible, stable transformation system generally applicable in a wild-type background in many fungi has strongly hampered molecular-biological research on such organisms.

Current transformation techniques for fungi have included a combination of $CaCl_2$ and polyethylene glycol (PEG), electroporation, and particle bombardment to introduce DNA into protoplasts, mycelium, or spores. These have been either without success, or not reproducible. The lack of a practical gene transfer system is the single largest obstacle precluding the use of molecular approaches for the genetic improvement of mushrooms. Despite considerable interest in the development of a transformation scheme, no method is in general use today, due to low efficiency or lack of utility and convenience.

In recent approaches, several fungi, including *A. bisporus*, have been transformed using an *Agrobacterium*-based transformation system. Although these methods are more convenient than the existing protoplast-based schemes, they have thus far suffered from a comparably low efficiency of transformation using complicated systems.

For example, Gouka et. al. describe a transformation procedure for targeted homologous recombinations in fungi, (Gouka et. al. Nature Biotechnology Vol 17 June 1999, "Transformation of *Aspergillus awamori* by *Agrobacterium tumefaciens*-mediated homologous recombination" pp 598–601). According to this procedure a specifically engineered *A. awamori* recipient strain containing a 3'-deleted nonfunctional pyrG gene and an *Agrobacterium* strain containing a binary vector suitable for restoring the pyrG gene by recombination are used. Homologous recombination between the repair construct and the recipient host result in restoration of functional pyrG gene and integration of the vector at the pyrG locus. The paper reported a high of 150 transformants per $10^7$ conidia.

De Groot et. al report yet another *Agrobacterium*-based method of transforming filamentous fungi, (De Groot et. el. Nature Biotechnology Vol 16 September 1998, "*Agrobacterium tumefaciens*-mediated transformation of filamentous fungi" pp. 839–842). This paper investigated the ability of *Agrobacterium* to transfer T-DNA to the *A. awamori* protoplasts (vegetative cells with the cell walls removed) and conidia. The transformation frequency varied from approximately 300 to 7200 transformants per $10^7$ protoplasts, which was up to 600 times higher than PEG transformation rates. When conidia were used, the transformation frequency varied from 1000 to 9000 transformants per $10^7$ conidia. Vegetative mycelial tissue was also used.

Other fungi transformation schemes are disclosed in WO95/02691 and WO98/45455. All of these have focused on transformation using protoplasts, spores, and vegetative mycelium as the recipient tissue.

As can be seen from the foregoing, there is a continuing need in the art for development of effective, convenient, and expeditious fungal transformation systems.

It is thus an object of the present invention to provide a transformation system for fungi that will accomplish the foregoing need.

A further object of this invention is to provide mechanisms for application of transgenic techniques such as those applied to bacteria, non-filamentous fungi (yeast), plants, and animals to increase yield, disease, and pest resistance, product quality, shelf life, or culinary, nutritional, or medicinal value, to produce commercially, or other such protocols.

It is yet another object of the invention to provide polynucleotide constructs, vectors, transformed cells for use in such transgenic protocols.

A further object of the present invention is to provide genetic constructs for expression of or inhibition of gene products in filamentous fungi.

Other objects of the invention will become apparent from the description of the invention that follows.

SUMMARY OF THE INVENTION

The improved transformation method described herein provides a practical method for using transgenic technology in the genetic improvement of filamentous fungi, and represents an important tool for the molecular genetic analysis of biological processes in these organisms. Further, the method enables the genetic modification of fungi to serve as biofermentors for the mass-scale production of commercially-important products, as for one example, human growth hormone. Additionally, the transformation protocol, with modifications to the choice of promoter and strain of *Agrobacterium*, is applicable to all fungal species that bear fleshy fruit bodies, and may be optimized by selection of strain of *Agrobacterium* or promoter. Examples of filamentous fungi useful for the invention include members of the phyla Basidoiomycota and Ascomycota as follows: *Coprinus* spp., *Coriolus* spp., *Agaricus* spp. including the species *bisporus, Flammulina velutipes, Lentinula edodes, Morchella* spp., *Phanerochaete chrysosporium, Pleurotus ostreatus, Schizophyllum commune*, and *Tricholoma matsutake*, among others.

Traditional transgenic techniques for fungi use protoplasts, vegetative mycelium, or spores as the recipient cell or tissue type. Applicants have surprisingly found that when the sexual reproductive structure tissue, that is the fruit body, is used, preferably comprising gill tissue, transformation rates are dramatically improved. The use of this tissue in any type of fungal transgenic protocol as described herein comprises the broadest aspect of the invention.

In a preferred embodiment, *Agrobacterium*-mediated transformation is used.

Applicants have devised a highly efficient, convenient, and expeditious genetic transformation system for filamentous fungi such as *A. bisporus*. The preferred method uses an *Agrobacterium*-mediated transformation protocol. The critical features of this protocol include co-cultivation of the bacterium with fruit body tissue instead of basidiospores. In a preferred embodiment, even higher transformation efficiencies were observed with the use of a homologous promoter in the polynucleotide expression construct, to drive gene expression. This method offers new prospects for the genetic improvement of commercially-important mushroom species as well as other filamentous fungal species, and potentiates the use of genetically-modified mushrooms as biofermentors for the mass production of commercially-valuable products. The methods of the invention provided up to a 92% efficiency of transformation (% of the tissue pieces regenerating colonies) based on antibiotic (hygromycin) resistance. This is six to seven orders of magnitude higher than the previously reported *Agrobacterium*-mediated transformation method for *A. bisporus* (~0.00003%). Moreover, transformants were recovered in as little as 7 days by the invention disclosed herein compared to 4–5 weeks for the method that was originally described.

With the transformation method of the invention, genetic engineering techniques known in the art and routinely applied to bacteria, non-filamentous fungi, plants, and animals can be used to genetically manipulate filamentous fungi for ease of cultivation or production, improved culinary, medicinal, or nutritional value, or production of recombinant proteins for harvest.

The invention further comprises novel compositions including protein products isolated from such transgenic fungi. Also included are expression constructs, for use in this procedure as well as transformed cells, vectors, and transgenic fungi incorporating the same.

The fruit body transformation protocol of the invention has a vastly superior practicality, offering a higher effective efficiency and greater convenience than other Agrobacterium-mediated transformation methods, and also being more expeditious.

Definitions

Various terms relating to the compositions and methods of the present invention are used herein above and also throughout the specification and claims and unless otherwise indicated shall have the meaning specified herein.

Various units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

As used herein the term "Agrobacterium" shall be intended to include any bacterial species and its conservatively modified variants that is capable of infecting a desired fungal cell. The Agrobacterium tumefaciens Ti plasmid is described herein, but the invention is not so limited. The choice of particular bacterial vector involves no more than routine optimization of parameters by those of skill in the art. Other bacteria may be used and are available to those of skill in the art through sources such as Genbank.

An "antisense oligonucleotide" is a molecule of at least 6 contiguous nucleotides, preferably complementary to DNA (antigene) or RNA (antisense), which interferes with the process of transcription or translation of endogenous proteins so that gene products are inhibited.

A "cloning vector" is a DNA molecule such as a plasmid, cosmid, or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include those that provide resistance to antibiotics such as hygromycin, tetracycline, or ampicillin.

A "coding sequence" or "coding region" refers to a nucleic acid molecule having sequence information necessary to produce a gene product, when the sequence is expressed.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid that encodes a polypeptide of the present invention is implicit in each described polypeptide sequence and is within the scope of the present invention.

As to amino acid sequences, one of skill will recognize that individual substitutions, deletions, or additions to a nucleic acid, peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
 1) Alanine (A), Serine (S), Threonine (T);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V); and
 6) Phenylalanine (F), Tyrosine (Y), Tryptophan (W). See also, Creighton (1984) Proteins W.H. Freeman and Company.

The term "co-suppression" is a method of inhibiting gene expression in organisms wherein a construct is introduced to an organism. The construct has one or more copies of sequence that is identical to or that shares nucleotide homology with a resident gene.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium Mycoplasma capricolum, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both plant and fungi species, sequences can be modified to account for the specific codon preferences and GC content preferences as these preferences have been shown to differ, as described in the references cited herein.

The term "expression" refers to biosynthesis of a gene product. Structural gene expression involves transcription of the structural gene into mRNA and then translation of the mRNA into one or more polypeptides.

An "expression vector" is a DNA molecule comprising a gene that is expressed in a host cell. Typically, gene expression is placed under the control of certain regulatory elements including promoters, tissue specific regulatory elements, and enhancers. Such a gene is said to be "operably linked to" the regulatory elements.

As used herein, the term "fruit body" is intended to include tissue or cells from any of the sexual reproductive structure tissues from a fungus, other than vegetative mycelium and spores, including the cap, stem, gill, veil, volva, etc.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

As used herein the term "high stringency" shall mean conditions or hybridization equivalent to the following: hybridized for 12 hours at 42° C. in a buffer containing 50% formamide, 5×SSPE, 2% SDS, 10×Denhardt's solution, and 100 μg/ml salmon sperm DNA, and washing with 0.1×SSC, 0.1% SDS at 55° C. and exposed to Kodak X-Omat AR film for 4 days at −70° C.

By "host cell" is meant a cell that contains a vector and supports the replication and/or expression of the vector. Host cells may be prokaryotic cells such as *E. coli*, or eukaryotic cells such as fungi, insect, amphibian, or mammalian cells. Preferably, the host cells are fungal cells.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "polynucleotide construct" or "DNA construct" is sometimes used to refer to an expression construction. This also includes, however, antisense oligonucleotides or nucleotides designed for co-suppression of native host cell sequences or extrinsic sequences corresponding, for example, to those found in viruses.

The term "operably linked" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g. enhancers) in an expression vector.

Transcriptional and translational control sequences are DNA regulatory sequences, such as promoters, enhancers, polyadenylation signals, terminators, and the like, that provide for the expression of a coding sequence in a host cell.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, phosphorylation, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation, which do not occur naturally. Circular, branched, and branched circular polypeptides may be synthesized by a non-translation natural process and by entirely synthetic methods, as well. Further, this invention contemplates the use of both the methionine-containing and the methionine-less amino terminal variants of the protein of the invention. With respect to a protein, the term "N-terminal region" shall include approximately 50 amino acids adjacent to the amino terminal end of a protein.

The terms "promoter", "promoter region", or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase. The term promoter includes the essential regulatory features of said sequence and may optionally include a long terminal repeat region prior to the translation start site.

A "recombinant host" may be any prokaryotic or eukaryotic cell that contains either a cloning vector or an expression vector. This term also includes those prokaryotic or eukaryotic cells that have been genetically engineered to contain the clone genes in the chromosome or genome of the host cell.

The term "reporter gene" refers to a gene that encodes a product that is easily detectable by standard methods, either directly or indirectly.

The term "selectable marker gene" refers to a gene encoding a product that, when expressed, confers a selectable phenotype such as antibiotic resistance on a transformed cell.

With respect to oligonucleotides or other single-stranded nucleic acid molecules, the term "specifically hybridizing" refers to the association between two single-stranded nucleic acid molecules of sufficiently complementary sequence to permit such hybridization under pre-determined conditions generally used in the art i.e., conditions of stringency (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "structural gene" is a DNA sequence that is transcribed into messenger RNA (mRNA), which is then translated into a sequence of amino acids characteristic of a specific polypeptide.

A "vector" is a replicon, such as plasmid, phage, cosmid, or virus to which another nucleic acid segment may be operably inserted so as to bring about the replication or expression of the segment.

DESCRIPTION OF FIGURES

The patent file contains at least one drawing executed in color. Copies of this patent with color drawings will be provided by the Office upon request and payment of the necessary fee.

DETAILED DESCRIPTION OF THE INVENTION

Figure 1:
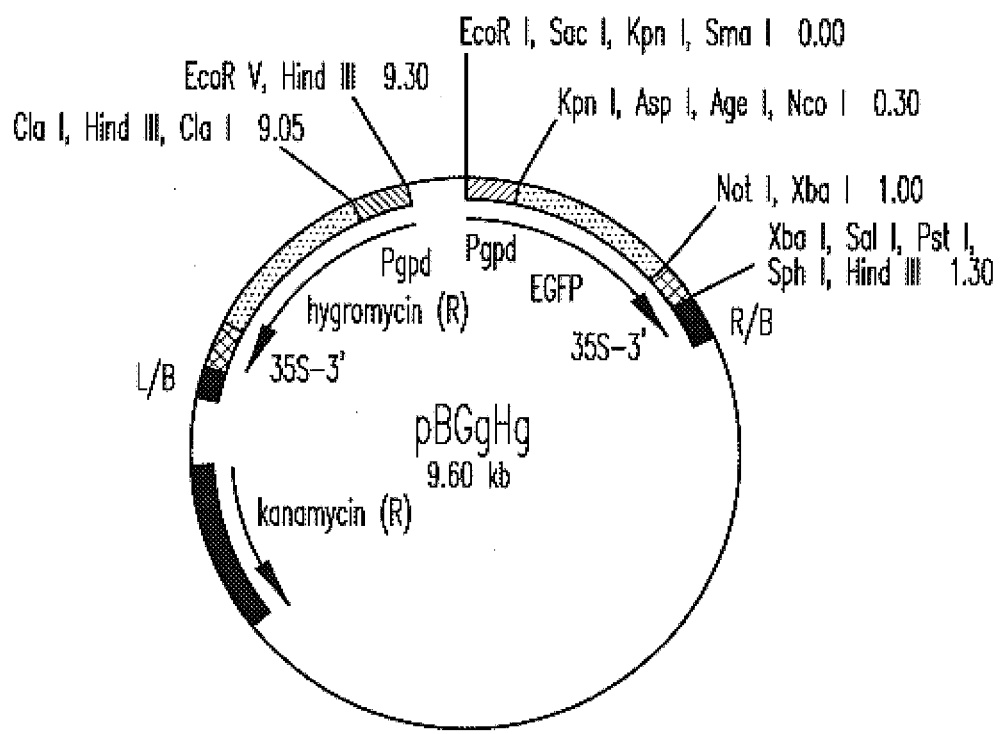
FIG. 1 depicts the organization of binary vector pBGgHg. pBGgHg is 9.6 kb in size and consists of a pCAMBIA 1300 backbone containing the kanamycin resistance (R) gene and the right border (R/B) and left border (L/B) sequences of *Agrobacterium* T-DNA. The hygromycin resistance (R) gene and enhanced green fluorescent protein gene (EGFP) are located between the border sequences and each is joined to the *A. bisporus* glyceraldehyde 3-phosphate dehydrogenase promoter (Pgpd) and cauliflower mosaic virus terminator (35S-3'). Shown are restriction enzyme sites with map distances in kb.

In its broadest sense the invention comprises the transformation of fungi using a transformation method known in the art and described herein using fruit body tissue, as opposed to protoplasts, spores, or vegetative mycelium as the recipient cells.

In a preferred embodiment the invention comprises the use of *Agrobacterium*-mediated transformation.

Methods for the use of *Agrobacterium*-based transformation systems have been described for many different plant species. *Agrobacterium tumefaciens* is a gram-negative soil bacterium that causes crown gall tumors at wound sites of infected plants. During tumor induction, *Agrobacterium* transfers part of its tumor inducing (Ti) plasmid, the T-DNA, which is flanked by 24 bp imperfect direct repeats, to plant cells. The T-DNA then integrates into the plant DNA at random position. The process of T-DNA transfer depends on the induction of a set of virulence, (vir) genes, which are also located on the Ti plasmid. The vir genes are induced by compounds secreted from wounded plant cells such as acetosyringone (AS). In fungal transformation schemes, AS or other vir inducers must be added to induce vir gene activity. The ease of use, its efficiency of transformation, and the precision of T-DNA integration has led to widespread use of this organism for gene transfer into plants, and the development of transformation protocols for important crops including cereals such as rice and maize.

Generally, strains of bacteria, such as *Agrobacterium tumefaciens*, are used for genetic transformation that transfer part of its Ti plasmid to plants during tumorigenesis. Typically, the *Agrobacterium* used harbors modified versions of the naturally occurring Ti plasmid in which the oncogenes and the opaline metabolism genes have been removed such that the DNA is transferred to the host cells without the subsequent formation of tumors. These methods involve the insertion within the borders of the Ti plasmid the DNA to be inserted into the cellular genome linked to a selection marker gene to facilitate selection of transformed cells. Bacteria and recipient plant tissues are cultured together to allow transfer of foreign DNA into plant cells then transformed plants are regenerated on selection media. Any number of different organs and tissues can serve as targets for *Agrobacterium*-mediated transformation as described specifically for members of the Brassicaceae. These include thin cell layers (Charest, P. J., et al, 1988, *Theor. Appl. Genet.* 75:438–444), hypocotyls (DeBlock, M., et al, 1989, *Plant Physiol.* 91:694–701), leaf discs (Feldman, K. A., and Marks, M. D., 1986, *Plant Sci.* 47:63–69), stems (Fry J., et al, 1987, *Plant Cell Repts.* 6:321–325), cotyledons (Moloney M. M., et al, 1989, *Plant Cell Repts.* 8:238–242) and embryoids (Neuhaus, G., et al, 1987, *Theor. Appl. Genet.* 75:30–36). *Agrobacterium*-mediated transformation has been shown effective in many species of both monocotyledonous as well as dicotyledonous plants. Recently, *Agrobacterium* transformation has been confirmed in yeast. See, Bundock, et. al. "Trans-kingdom T-DNA transfer from

*Agrobacterium tumufaciens* to *Saccharomyces cerevisiae*" The EMBO Journal vol. 14 no. 13 pp. 3206–3214, 1995. Interestingly, however, the transfer in yeast was shown to occur by a different mechanism than observed in plants. The authors conclude that the integration is predominately determined by host factors rather than the bacterium itself. This is important as depending on the particular host, integration may or may not occur depending on the host factors present. More recently, *Agrobacterium*-mediated transformation has been confirmed in *A. bisporus*, de Groot et al., but only with very low efficiency and a protracted procedure.

According to the invention, a polynucleotide construct to be introduced to a filamentous fungal cell by *Agrobacterium*, which acts as a vehicle for a transforming plasmid. Typically, the polynucleotide construct is inserted within the borders of a Ti plasmid containing functional vir genes, although the vir genes and polynucleotide need not be on the same plasmid.

Genetic transformation then occurs by simply incubating *Agrobacterium* with the fungal fruit body tissue cells. Subsequently, the bacterium is killed and the fruit body cells are allowed to regenerate under selective pressure to identify transformants.

Thus, the invention provides a transformed filamentous fungus obtainable by *Agrobacterium*-mediated transformation according to the invention not comprising any unwanted bacterial DNA sequence including a T-DNA border. Such transformed fungi can be used in a process for culturing a transformed fungus in order to produce a desired protein or specific nucleic acid sequence. Further, in accordance with the invention, short nucleic acid sequences, that may not encode a protein product, corresponding to some target gene (host or viral coded), might be expressed for the purpose of co-suppressive silencing. The invention also contemplates growing transgenic fungi for the mushrooms as a food, medicine, etc. and as a source of a desired protein (e.g., pharmaceutical production), as well as for the growth of vegetative mycelium as a source of a desired protein. Further, the protein may remain within the fungal cells requiring extraction, but the protein may also be secreted into the growth medium for recovery.

According to another embodiment of the invention a process is provided, in which the DNA fragment is randomly integrated in the fungal genome, as well as a transformed fungus obtainable by *Agrobacterium*-mediated transformation, which comprises one or more parts of T-DNA border sequences, and a process for culturing such transformed fungus in order to produce a desired protein or specific nucleic acid sequence.

The use of supervirulent *A. tumefaciens* strains is preferred, because they give a relatively high transformation frequency, such strains, the use thereof and vectors for making such strains are described in the literature; see Jin et al. (J. Bacteriology 169 (1987) 4417–4425 & Molecular Microbiology 7 (1993) 55–562), Raineri et al. (BIO/TECHNOLOGY 8 (January 1990) 33–38) and Ishida et al. (Nature Biotechnology 14 (1996) 745–750) for plant transformation, and Piers et al. (*Proc. Nat'l. Acad. Sci. USA*, 93 (1996) 1613–1618) for yeast transformation.

The transformation can be performed by a binary system where the vir genes act in trans or by co-integration with homologous recombination between a first plasmid and a wild-type Ti plasmid causing the oncogenes to be expelled from the plasmid in a similar way as known for plant transformation as discussed herein and known to those of skill in the art.

Production of a genetically modified fungal tissue either expressing or inhibiting expression of a structural gene combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the fungal species to be modified, the particular structural gene, promoter elements, and upstream elements used. Persons skilled in the art are able to select and use appropriate alternatives to achieve functionality. Culture conditions for expressing desired structural genes and cultured cells are known in the art. Also as known in the art, a number of fungal species are transformable and regenerable such that the whole fungus, including all vegetative and reproductive tissues such as the mycelium, fruit bodies, and spores, containing and expressing desired genes under regulatory control of the promoter molecules according to the invention may be obtained. As is known to those of skill in the art, expression in transformed fungi may be tissue specific and/or specific to certain developmental stages. Truncated promoter selection and structural gene selection are other parameters that may be optimized to achieve desired fungal expression or inhibition as is known to those of skill in the art and taught herein.

The following is a non-limiting general overview of molecular biology techniques that may be used in performing the methods of the invention.

The polynucleotide constructs of the present invention will share similar elements, which are well known in the art of molecular biology. For example, in each construct the DNA sequences of interest will preferably be operably linked (i.e., positioned to ensure the functioning of) to a promoter that allows the DNA to be transcribed (into an RNA transcript) and will comprise a vector that includes a replication system. In preferred embodiments, the DNA sequence of interest will be of exogenous origin in an effort to prevent co-suppression of the endogenous genes, unless co-suppression is the desired protocol.

Promoters

The constructs, promoters or control systems used in the methods of the invention may include a tissue specific promoter, an inducible promoter, or a constitutive promoter.

A large number of suitable promoter systems are available. For example, one constitutive promoter useful for the invention is the cauliflower mosaic virus (CaMV) 35S. It has been shown to be highly active in many prokaryotic and eukaryotic species.

Promoters (and other regulatory elements) may be heterologous (i.e., not naturally operably linked to a DNA sequence from the same organism). Promoters useful for expression in fungi are known in the art and can be inducible, constitutive, tissue-specific, derived from eukaryotes, prokaryotes, or viruses, or have various combinations of these characteristics.

In choosing a promoter to use in the methods of the invention, it may be desirable to use a tissue-specific or developmentally regulated promoter. A tissue-specific or developmentally regulated promoter is a DNA sequence that regulates the expression of a DNA sequence selectively in the cells/tissues critical to a particular developmental period and/or function in the fungus. Any identifiable promoter may be used in the methods of the present invention that causes expression in fungi and there are many such promoters available. It may also be advantageous to use an inducible promoter to provide expression of the construct during controlled periods.

An inducible promoter may also be used in the instant invention. See Ward et al. *Plant Mol. Biol.* 22: 361–366 (1993). Exemplary inducible promoters include, but are not limited to, that from the ACE1 system which responds to copper (Mett et al. *PNAS* 90: 4567–4571 (1993)); In2 gene from maize which responds to benzenesulfonamide herbicide safeners (Hershey et al., *Mol. Gen. Genetics* 227: 229–237 (1991) and Gatz et al., *Mol. Gen. Genetics* 243: 32–38 (1994)) or Tet repressor from Tn10 (Gatz et al., *Mol. Gen. Genet.* 227: 229–237 (1991). A particularly preferred inducible promoter is a promoter that responds to an inducing agent to which fungi do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88: 0421 (1991).

These and other such promoters are known and accessible through sources such as Genbank. In a preferred embodiment, the promoter is homologous to the recipient host cell species. For example, in the *A. bisporus* transformation protocol, an *A. bisporus* glyceraldehyde 3-phosphate dehydrogenase (GPD) promoter is used in the polynucleotide construct. Two examples of fungi specific promoters include, but are not limited to, the GPD promoters from the fungi *A. nidulans*, (Mattern et. al. 1988, Fungal Genetics Newsletter 35:25), and *A. bisporus*, (Harmsen et. al. 1992 Current Genetics 22:447–454).

It may also be desirable to include some intron sequences in the promoter constructs since the inclusion of intron sequences in the coding region may result in enhanced expression and specificity.

Additionally, regions of one promoter may be joined to regions from a different promoter in order to obtain the desired promoter activity resulting in a chimeric promoter. Synthetic promoters that regulate gene expression may also be used.

The expression system may be further optimized by employing supplemental elements such as transcription terminators and/or enhancer elements.

Other Regulatory Elements

In addition to a promoter sequence, an expression cassette or polynucleotide construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium* octopine synthase signal (Gielen et al., *EMBO J.* (1984) 3:835–846) or the nopaline synthase signal (Depicker et al., *Mol. and Appl. Genet.* (1982) 1:561–573).

Transport of protein produced by transgenes to a subcellular compartment such as the vacuole, peroxisome, glyoxysome, cell wall or mitochondrion, or for secretion into the apoplast or growth medium, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately located. The presence of a signal sequence directs a polypeptide to either an intracellular organelle or subcellular compartment or for secretion to the apoplast or into the external environment. Many signal sequences are known in the art.

Marker Genes

Recombinant DNA molecules containing any of the DNA sequences and promoters described herein may additionally contain selection marker genes that encode a selection gene product conferring on a cell resistance to a chemical agent or physiological stress, or confers a distinguishable phenotypic characteristic to the cells such that cells transformed with the recombinant DNA molecule may be easily selected using a selective agent. One such selection marker gene is neomycin phosphotransferase (NPT II), which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reaction (PCR) amplification is also used to identify the presence of a transgene or expression using reverse transcription-PCR amplification to monitor expression and PCR on genomic DNA. Other commonly used selection markers include the ampicillin resistance gene, the tetracycline resistance and the hygromycin (HPH) resistance gene. Transformed fungal cells thus selected can grow and develop into the vegetative mycelium, which will eventually yield the whole fungus, including the sexual reproductive structure (fruit body) and spores. It is to be understood that a selection marker gene may also be native to a fungus.

Proteins

With transgenic fungi according to the present invention, a foreign protein can be produced in commercial quantities. Thus, techniques for the selection and propagation of transformed fungi, which are well understood in the art, yield a plurality of transgenic fungi that are harvested in a conventional manner, and a foreign protein then can be extracted from a tissue of interest or from total biomass, or secreted into the growth medium (liquid or solid state) and then recovered. Protein extraction from plant and fungal biomass can be accomplished by known methods which are discussed, for example, by Heney and Orr, *Anal. Biochem.* 114: 92–6 (1981), and in the references cited herein.

For the relatively small number of transgenic fungi that show higher levels of expression, a genetic map can be generated, primarily via conventional Restriction Fragment Length Polymorphisms (RFLP), PCR analysis, and Simple Sequence Repeats (SSR), which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton, 1993). Map information concerning chromosomal location is useful for proprietary protection of a subject transgenic fungus. If unauthorized propagation is undertaken and crosses made with other germplasm, the map of the integration region can be compared to similar maps for suspect fungi, to determine if the latter have a common parentage with the subject fungi. Map comparisons would involve hybridizations, RFLP, PCR, SSR and sequencing, all of which are conventional techniques.

Likewise, by means of the present invention, agronomic genes can be expressed in transformed fungi. More particularly, fungi can be genetically engineered to express various phenotypes of agronomic interest. Exemplary genes implicated in this regard include, but are not limited to, those categorized below.

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*).

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt □-endotoxin gene. Moreover, DNA molecules encoding □-endotoxin genes can be purchased from American Type Culture Collection (Rockville, Md.), for example, under ATCC Accession Nos. 40098, 67136, 31995 and 31998.

(C) A lectin. See, for example, the disclosure by Van Damme et al., *Plant Molec. Biol.* 24: 25 (1994), who disclose the nucleotide sequences of several *Clivia miniata* mannose-binding lectin genes.

(D) A vitamin-binding protein, such as avidin. See PCT application US93/06487 the contents of which are hereby incorporated by. The application teaches the use of avidin and avidin homologues as larvicides against insect pests.

(E) An enzyme inhibitor, for example, a protease inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), and Sumitani et al., *Biosci. Biotech. Biochem.* 57: 1243 (1993) (nucleotide sequence of *Streptomyces nitrosporeus* alpha-amylase inhibitor).

(F) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(G) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

2. Genes that Confer Resistance to a Herbicide, for Example:

(A) A herbicide that inhibits the growing point or meristem, such as an imidazalinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP that can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

3. Genes that Confer or Contribute to a Value-Added Trait, Such as:

(A) Modified fatty acid metabolism, for example, by transforming a plant with an antisense gene of stearoyl-ACP desaturase to increase stearic acid content of the plant. See Knultzon et al., *Proc. Natl. Acad. Sci. USA* 89: 2624 (1992).

(B) Decreased phytate content (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(2) A gene could be introduced that reduces phytate content. In maize, this, for example, could be accomplished, by cloning and then reintroducing DNA associated with the single allele which is responsible for maize mutants characterized by low levels of phytic acid. See Raboy et al., *Maydica* 35: 383 (1990).

(C) Modified carbohydrate composition effected, for example, by transforming plants with a gene coding for an enzyme that alters the branching pattern of starch. See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* □-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley alpha-amylase gene), and Fisher et al., *Plant Physiol.* 102: 1045 (1993) (maize endosperm starch branching enzyme II).

Antisense or co-suppressive techniques may also be used according to the references disclosed herein.

Transformation

Traditional transformation techniques may be used in addition to *Agrobacterium* transfection. Other methods that have been employed for introducing recombinant molecules into plant cells involve mechanical means such as direct DNA uptake, liposomes, electroporation (Guerche, P. et al, 1987, *Plant Science* 52:111–116), and micro-injection (Neuhaus, G., et al, 1987, *Theor. Appl. Genet.* 75:30–36). The possibility of using microprojectiles and a gun or other device to force small metal particles coated with DNA into cells has also received considerable attention (Klein, T. M. et al., 1987, *Nature* 327:70–73).

It is often desirable to have the DNA sequence in homozygous state, which may require more than one transformation event to create a parental line; requiring transformation with a first and second recombinant DNA molecule both of which encode the same gene product. It is further contemplated in some of the embodiments of the process of the invention that a fungal cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual fungi or fungal lines containing different DNA sequences or recombinant DNA molecules preferably the DNA sequences or the recombinant molecules are linked or located on the same chromosome, and then selecting from the progeny of the cross, fungi containing both DNA sequences or recombinant DNA molecules.

Expression of recombinant DNA molecules containing the DNA sequences and promoters described herein in transformed fungi cells may be monitored using northern blot techniques and/or Southern blot techniques known to those of skill in the art.

The regenerated fungi are transferred to standard growing media (e.g., solid or liquid nutrient media, grain, vermiculite, compost, peat, wood, wood sawdust, straw, etc.) and grown or cultivated in a manner known to those practiced in the art.

After the polynucleotide is stably incorporated into regenerated transgenic fungi, it can be transferred to other fungi by sexual crossing. Any of a number of standard breeding techniques can be used, depending upon the species to be crossed.

It may be useful to generate a number of individual transformed fungi with any recombinant construct in order to recover fungi free from any positional effects. It may also be preferable to select fungi that contain more than one copy of the introduced recombinant DNA molecule such that high levels of expression of the recombinant molecule are obtained.

As indicated above, it may be desirable to produce fungal lines that are homozygous for a particular gene if possible in the particular species. In some species this is accomplished by the use monosporous cultures. By using these techniques, it is possible to produce a haploid line that carries the inserted gene and then to double the chromosome number either spontaneously or by the use of colchicine. This gives rise to a fungus that is homozygous for the inserted gene, which can be easily assayed for if the inserted gene carries with it a suitable selection marker gene for detection of fungi carrying that gene. Alternatively, fungi may be self-fertilized, leading to the production of a mixture of spores that consists of, in the simplest case, three types, homozygous (25%), heterozygous (50%) and null (25%) for the inserted gene. Although it is relatively easy to score null fungi from those that contain the gene, it is possible in practice to score the homozygous from heterozygous fungi by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the fungi was homozygous for the inserted gene, all of the subsequent fungal lines from the selfed individual will contain the gene, while if the fungus was heterozygous for the gene, the generation grown from the selfed seed will contain null fungal lines. Therefore, with simple selfing one can select homozygous fungal lines that can also be confirmed by Southern blot analysis.

Creation of homozygous parental lines makes possible the production of hybrid fungus and spores that will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The following example is intended to further illustrate the invention and are not limit the invention in any way. The examples and discussion herein may specifically reference *A. bisporus*, however the teachings herein are equally applicable to any other fungus, preferably filamentous fungi that bear fleshy fruit bodies.

EXAMPLE 1

Fruit bodies of six commercial hybrid strains of *A. bisporus* were grown. Vegetative mycelial cultures of the strains were derived from commercial grain spawn, and maintained on potato dextrose yeast agar. Genomic DNA was isolated from fruit bodies (1–3 g) and broth cultures (100 mg of mycelium) by conventional phenol extraction in the presence of lithium chloride and ethanol precipitation.

Publically available strains AGL-1, EHA-105, and GV3850 of *A. tumefaciens* were obtained. The *Escherichia coli* HPH (hygromycin B phosphotranferase) gene, along with *Aspergillus nidulans* trpC promoter were also provided. The binary vector pCAMBIA 1300 (CAMBIA, Canberra, Australia), *Aequorea victoria* enhanced green fluorescent protein (EGFP) gene, and CaMV 35S promoter and terminator also were obtained from public sources. The promoter for the GPD gene of *A. bisporus* was obtained by PCR amplification using the published sequence data.

Our binary plasmid vector (9.6 kb), designated pBGgHg, consisted of a pCAMBIA 1300 backbone containing the HPH and EGFP genes, each of which was joined to the CaMV 35S terminator and controlled by the GPD promoter from *A. bisporus* (FIG. 1). In order to construct vector pBGgHg, intermediate plasmid pEGFP.g was generated by excising the CaMV 35S promoter from PE2113-EGFP with HindIII and KpnI and inserting the GPD promoter sequence obtained by PCR amplification with primers gpd-FH and gpd-RK containing HindIII and KpnI restriction sites, respectively. Intermediate plasmid pHph.g was designed from PCSN44 by excising the trpc promoter with HindIII and ClaI and blunt-end ligating to the GPD promoter derived by PCR amplification with primers gpd-FH and gpd-RC. Intermediate plasmid pBHg was made by digesting pCAMBIA 1300 with BstXI and XhoI to remove the HPH gene and CaMV 35S promoter and inserting by blunt-end ligation the HPH gene and GPD promoter, which was excised from pHph.g using BamHI. Finally, pBGgHg was constructed by excising the EGFP gene with the GPD promoter from pEGFP.g using EcoRI and HindIII and inserting this fragment by blunt-end ligation at the BamHI site in pBHg.

Southern blot analysis was carried out with a $^{32}$P-labeled ~1 kb fragment of HPH gene as a probe. PCR analysis was done using primers gpd-FH ('5-GAAGAAGCTTTAAGAGGTCCGC-3') and hyg-R (5'-GGCGACCTCGTATTGGGAATC-3'), which defined an ~970 sequence spanning the GPD promoter and HPH gene.

Next, the original *Agrobacterium*-mediated transformation method for *S. cerevisiae*, as modified for the use of spores of filamentous fungi, was adopted in the present invention except that fruit body tissue, instead of basidiospores of *A. bisporus*, was co-cultivated with *A. tumefaciens*. This had a surprising major impact on the effective transformation efficiency. Fruit bodies were selected that were nearing maturity, but with the veil intact and the gills unexposed ("mature gill" or "gill"). Fruit bodies were surface sterilized by soaking in a 10% commercial sodium hypochlorite solution (bleach) and then rinsing them with sterile distilled water. Using a sterile scapel, the veil was removed, and the exposed gill tissue was excised and sectioned into 2–5 mm square pieces for use.

In some experiments, where indicated, the fleshy tissue derived from the caps and stems of fruit bodies was used as a tissue source for transformation ("non-gill tissue"). In yet another variation on the basic protocol, and where indicated, transformation was carried out on undeveloped gill tissue sampled from immature fruit bodies between the pin to button stage of development ("immature gill").

In all cases, tissue pieces were vacuum-infiltrated with the bacterial suspension in induction medium for several minutes, until the air had been purged from the tissue, and then transferred to a piece of sterile 3MM Whatman filter paper that had been overlaid on co-cultivation medium. Tissue pieces were incubated on this medium for 3–4 days before transferring to selection medium containing 30 µg/ml hygromycin. Mycelial cultures growing on this medium were subsequently transferred to new selection medium containing 30–50 µg/ml hygromycin. After regeneration on this medium, cultures could be grown in a liquid nutrient medium to obtain sufficient mycelial biomass to carry out molecular analyses (Southern and northern blot analyses, PCR, RT-PCR, etc.). Also, cultures could be grown on sterilized cereal grain (spawn) for the inoculation of compost in the production of fruit bodies by conventional methods. A detailed summary of the fruit body transformation protocol is attached (Table 1.).

TABLE 1

Fruit body Protocol for Agrobacterium-mediated Transformation of Mushrooms (Agaricus bisporus)

General Comments: In preparation, autoclave distilled water, filter paper for co-cultivation plates, flasks for growing Agrobacterium, and side-arm flasks for vacuum infiltration. Prepare LB medium, (LB) plates, minimal medium (MM), induction medium (IM), co-cultivation medium (CC) plates, and selection medium (SM) plates. Where "filter sterilized" is indicated, reagents were passed through a 0.2µ membrane filter. Store all reagents at 6□C. Note that MES and K-buffer may precipitate and so, before use, these reagents should be warmed until completely dissolved. Just before use, prepare fresh AS from the crystalline solid.

1. Sample Agrobacterium (strain AGL-1) from cultures stored in 10% glycerol at −80° C. and plate on LB medium containing 50 µg/ml kanamycin. Incubate the plate for two days at 28° C.
2. Recover Agrobacterium from the plate with a sterile transfer loop and inoculate 100 ml of MM containing 50 µg/ml kanamycin in a 250-ml flask.
3. Grow the bacterial culture overnight at 28° C. with constant gyratory shaking at 250 rpm to an O.D.$_{600}$ = 0.6–0.8. Sediment the bacteria by centrifugation at 2000 × g for 15 minutes.
4. Resuspend the bacteria in 100 ml of IM. Induce the bacteria by gyratory shaking at 100 rpm for 3–6 hrs at 25□C. For highly efficient transformation, it is important to prepare the IM just before use with fresh AS (i.e., directly from the solid).
5. Surface sterilize the fruit bodies by soaking them in 10% sodium hypochlorite solution for ~1 minute, and then rinsing three times with autoclaved distilled water. Select fruit bodies with intact veils to insure greater sterility of the gill tissue.
6. Using a sterile scapel, remove the veil from the fruit body, excise the exposed gills, and section the gill tissue into 2–5 mm pieces.
7. Transfer the 100 ml of the AS-induced Agrobacterium suspension from the shaker and 100–150 pieces of the sectioned gill tissue to a sterile 250-ml side-arm flask. Apply a vacuum to remove air from the intercellular spaces. Look for air bubbles emanating from the tissue pieces. Continue vacuuming until the TABLE 1-continued Fruit body Protocol for Agrobacterium-mediated Transformation of Mushrooms (Agaricus bisporus)

many of the tissue pieces settle to the bottom of the flask.
8. Decant the Agrobacterium suspension from the flask. Transfer the tissue pieces to petri plates containing CC medium overlaid with a piece of sterilized Whatman 3MM filter paper. Care should be taken to remove air bubbles that have become trapped between the paper and the medium. Also, the tissue pieces should be uniformly distributed on the surface of paper to maximize their contact with the medium. Seal the plates with plastic wrap, and incubate for 3–4 days at 20–24□C.
9. Transfer the fruit body tissue pieces to petri plates of SM containing 30 µg/ml hygromycin. Seal the plates with plastic wrap and incubate at 22–24□C. in the dark. Putative hygromycin-resistant colonies of A. bisporus may appear growing at the margins of the tissue pieces after 7 days of incubation, and continue to appear for ~30 days.
10. Transfer the hygromycin-resistant colonies to fresh SM plates containing 30–50 µg/ml hygromycin. Seal and incubate the plates as before.
11. Putatively-transformed mycelial cultures can be subjected to molecular analysis for authentication (Southern and northern hybridization analyses, PCR, RT-PCR, etc.), and used to prepare spawn for the production of fruit bodies.

Reagents/Media for Transformation

LB Medium (LB) (Petri Plates)

10 g NaCl 10 g tryptone 5 g yeast extract 15 g agar

Adjust to a final volume of 1 L with distilled water. Autoclave for 20 min. Pour plates as desired.

Minimal Medium (MM) (All Solutions are Filter Sterilized)

10 ml K-buffer, pH 7.0:
  200 g/L $K_2HPO_4$
  145 g/L $KH_2PO_4$ 20 ml M-N:
  30 g/L $MgSO_4.7H_2O$
  15 g/L NaCl 1 ml 1% $CaCl_2.2H_2O$ (w/v)

10 ml 20% glucose (w/v)

10 ml 0.01% $FeSO_4$ (w/v)

5 ml element stock:
  100 mg/L $ZnSO_4.7H_2O$
  100 mg/L $CuSO_4.5H_2O$
  100 mg/L $H_3BO_3$
  100 mg/L $MnSO_4.H_2O$
  100 mg/L $Na_2MoO_4.2H_2O$ 2.5 ml 20% $NH_4NO_3$ (w/v)

50 µg/ml kanamycin

Adjust to a final volume of 1 L with autoclaved distilled water.

Induction Medium (IM) (All Solution are Filter Sterilized)

0.8 ml 1.25 M K-buffer:
  170 g/L $K_2HPO_4$ Adjust to pH 4.9 with phosphoric acid 20 ml M-N:

1 ml 1% $CaCl_2.2H_2O$ 5 ml element stock (see MM above)

2.5 ml 20% $NH_4NO_3$ (w/v)

10 ml 50% glycerol 40 ml 1M MES:
  39.04 g $C_6H_{13}NO_4S$ or 42.64 g $C_6H_{13}NO_4S.H_2O$;
  Adjust to pH 5.5 with NaOH
10 ml 20% glucose (w/v)
100 mM acetosyringone (dissolve 0.196 g in 2–3 ml of 70% ETOH and use the entire volume; prepare fresh each use)
50 µg/ml kanamycin
Adjust to a final volume of 1 L with autoclaved distilled water. Store all
Co-cultivation Medium (CC) (Petri Plates) (All Solutions are Filter Sterilized)
  IM and containing:
  20% glucose
  1.5% agar
Autoclave for 20 min. Pour plates as desired.
Selection Medium (SM) (Petri Plates)
  20 g Malt extract
  2.1 g MOPS
  1.5% agar
Adjust to pH 7.0 with KOH
Adjust to 1 L with distilled water
Autoclave for 20 min, cool, and add the following antibiotics (filter sterilized):
  30 or 50 µg/ml hygromycin
  200 µM cefotaxim
  100 µg/ml moxalactum Unless stated otherwise, all experiments described herein involved the use of gill tissue from mature fruit bodies, *Agrobacterium tumefaciens* strain AGL-1 carrying binary plasmid vector pBGgHg, a 2–6 hr induction period in 200 µM AS, a 3 day co-cultivation period, and selection on a 30 µg/ml hygromycin medium for 28 days. Also, in the initial experiments, the AS stock was prepared in 70% ethanol and stored at −20☐ C. for weeks to months for use. However, in later experiments, the AS was prepared fresh in 70% ethanol for each experiment, as this led to consistently high transformation efficiencies.

Control treatments consisted of either tissue pieces that were vacuum infiltrated with induction medium alone or infiltrated with bacteria that had not been induced with AS.

Figure 2:
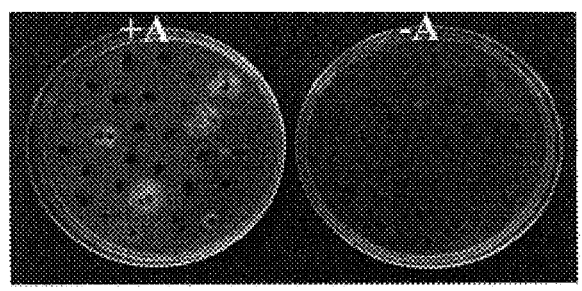
FIG. 2 illustrates selection of putative hygromycin resistant transformants of *Agaricus bisporus*. Pieces of fruit body gill tissue were co-cultivated for 3 days with (A+) and without (A−) *Agrobacterium tumefaciens* strain AGL-1 carrying the vector pBGgHg containing the *A. bisporus* GPD promoter and HPH gene construct. Shown is the appearance of the cultures after 2 weeks on selection medium with 30 μg/ml of hygromycin.
Figure 3:
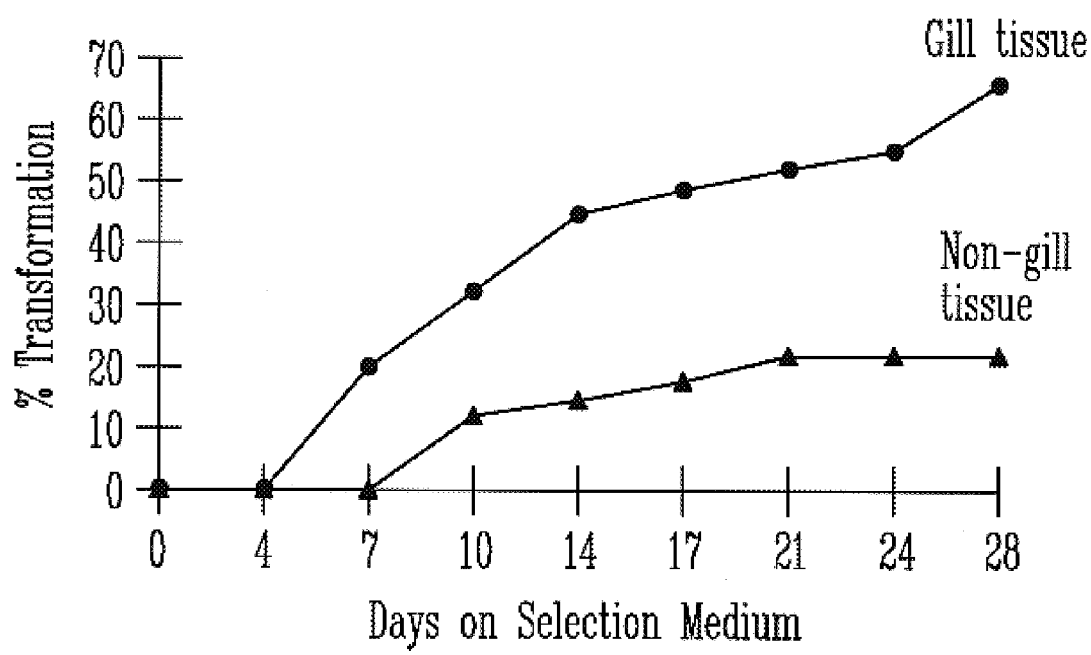
FIG. 3 depicts the time-course for the selection of hygromycin resistant transformants. Gill tissue and non-gill tissue from fruit bodies were co-cultivated for 3 days with *Agrobacterium tumefaciens* AGL-1 carrying the vector pBGgHg. Selection of antibiotic resistant transformants was carried out on selection medium containing 30 μg/ml of hygromycin.

Hygromycin-resistant colonies of *A. bisporus* appeared at the margins of the tissue pieces beginning as early as 7 days of incubation on selection medium (FIGS. 2 & 3). The methods of the invention provided an 8 to 92% efficiency of transformation (% of the tissue pieces regenerating colonies) between experiments based on hygromycin resistance. This is six to seven orders of magnitude higher than the previously reported *Agrobacterium*-mediated transformation method for *A. bisporus* (~0.00003%). The fruit body transformation protocol of the invention has a vastly superior practicality, offering a higher effective efficiency, greater convenience, and being considerably more expeditious than the original *Agrobacterium*-mediated transformation method described for *A. bisporus*.

The choice of promoter, strain of *A. tumefaciens*, and type of fruit body tissue were varied to isolate preferred embodiments of the invention. In a series of three experiments comparing constructs of the HPH gene and the *A. bisporus* GPD, *Aspergillus nidulans* trpC, or CaMV 35S promoter, only the vector with the homologous promoter (i.e. *A. bisporus* GPD) transformed *A. bisporus* with a high efficiency (Table 2.)

Thus, it is likely that promoters for other genes from *A. bisporus* could be substituted for the *A. bisporus* GPD promoter with similar efficiencies.

TABLE 2

Effect of the source of the promoter on the transformation of *Agaricus bisporus*

| Source of Promoter | Transformation Efficiency[a] | | |
|---|---|---|---|
| | Exp. I | Exp. II | Mean |
| *Agaricus bisporus* GPD | 7/50 (14%) | 3/50 (16%) | 15% |
| *Aspergillus nidulans* trpC | 1/50 (2%) | 0/50 (0%) | 1% |
| CaMV 35S | 0/50 (0%) | 0/50 (0%) | 0% |

[a]Expressed as the number of hygromycin-resistant colonies obtained/number of fruit body tissue pieces plated on selection medium containing 30 µg/ml hygromycin Of the three bacterial strains examined, only AGL-1 and EHA-105, but not GV3850, transformed *A. bisporus*, each averaging ~23% efficiency in two experiments (Table 3).

TABLE 3

Effect of the strain of *Agrobacterium tumefaciens* on the transformation of *Agaricus bisporus*

| Agrobacterium Strain | Transformation Efficiency[a] | | |
|---|---|---|---|
| | Exp. I | Exp. II | Mean |
| AGL-1 | 7/50 (14%) | 16/50 (32%) | 23% |
| EHA-105 | 4/50 (8%) | 18/50 (36%) | 22% |
| GV3850 | 0/50 (0%) | 0/50 (0%) | 0% |

[a]Expressed as the number of hygromycin-resistant colonies obtained/number of fruit body tissue pieces plated on selection medium containing 30 µg/ml hygromycin Fruit body pieces composed of gill tissue as well as non-gill tissue derived from the stem and cap from fruit bodies could be used to transform *A. bisporus*, but the gill tissue provided the highest efficiency of transformation (a mean of 57% compared to 17%) (Table 4). Not only did gill tissue provide higher efficiencies than non-gill tissue, but transformants appeared earlier on the antibiotic selection medium. Hygromycin-resistant transformants derived from gill tissue developed as soon as 7 days after incubation on selection medium compared to 10 days or longer for non-gill tissue-derived transformants (FIG. 3).

TABLE 4

Effect of the type of fruit body tissue on the transformation of *Agaricus bisporus*

| Type of Fruit Body Tissue | Transformation Efficiency[a] | | | | |
|---|---|---|---|---|---|
| | Exp. I | Exp. II | Exp. III | Exp. IV | Mean |
| Gill | 23/50 (46%) | 44/50 (88%) | 15/50 (30%) | 32/50 (64%) | 57% |
| Non-gill | 5/50 (10%) | 10/50 (20%) | 8/50 (16%) | 11/50 (22%) | 17% |

[a]Expressed as the number of hygromycin-resistant colonies obtained/number of fruit body tissue pieces plated on selection medium containing 30 µg/ml hygromycin Co-cultivation of *A. tumefaciens* with gill tissue from mature fruit bodies as well as undeveloped gills from immature fruit bodies, with either 200 µM or 400 µM AS used during the induction step, provided comparable efficiencies of transformation with means ranging from 53% to 82% (Table 5).

TABLE 5

Effect of the developmental state of the fruit body gill tissue on the transformation of *Agaricus bisporus*

| Type of Fruit Body Tissue | AS Conc.[b] | Transformation Efficiency[a] | | | |
|---|---|---|---|---|---|
| | | Exp. I | Exp. II | Exp. III | Mean |
| Mature Gill | 200 µM | 46/50 (92%) | 30/50 (60%) | 41/50 (82%) | 78% |
| | 400 µM | 28/50 (56%) | — | — | 56% |
| Immature Gill | 200 µM | 44/50 (88%) | 3/50 (6%) | 33/50 (66%) | 53% |
| | 400 µM | 41/50 (82%) | — | — | 82% |

[a]Expressed as the number of hygromycin-resistant colonies obtained/number of fruit body tissue pieces plated on selection medium containing 30 µg/ml hygromycin
[b]Concentration of acetosyringone (AS) used for induction of the bacterium Induction of the bacterium with AS for periods ranging from 2 to 24 hours resulted in high transformation efficiencies averaging in four experiments from 30% to 48% (Table 6).

TABLE 6

Effect of induction time of *Agrobacterium tumefaciens* with acetosyringone on the transformation of *Agaricus bisporus*

| Induction Time (hr) | Efficiency of Transformation[a] | | | | |
|---|---|---|---|---|---|
| | Exp. I | Exp. II | Exp. III | Exp. IV | Mean |
| 0 | 0/50 (0%) | 0/50 (0%) | 0/50 (0%) | 0/50 (0%) | 0% |
| 2 | — | — | 9/50 (22%) | 30/50 (60%) | 41% |
| 3 | 23/50 (46%) | 14/50 (28%) | 32/50 (64%) | 27/50 (54%) | 48% |
| 6 | 17/50 (34%) | 4/50 (8%) | 13/50 (26%) | 40/50 (80%) | 37% |
| 24 | 4/50 (8%) | 26/50 (52%) | — | — | 30% |

[a]Expressd as the number of hygromycin-resistant colonies obtained/number of fruit body tissue pieces plated on selection medium containing 30 µg/ml hygromycin Induction of *A. tumefaciens* with AS at 20° C. and 25° C. provided high transformation efficiencies of 48% and 60%, respectively (Table 7).

TABLE 7

Effect of temperature during induction of *Agrobacterium tumefaciens* on the transformation of *Agaricus bisporus*

| Induction Temperature (° C.) | Transformation Efficiency[a] |
|---|---|
| 20 | 24/50 (48%) |
| 25 | 30/50 (60%) |

[a]Expressed as the number of hygromycin-resistant colonies obtained/number of fruit body tissue pieces plated on selection medium containing 30 µg/ml hygromycin Efficient transformation of *A. bisporus* resulted when fruit body tissue was co-cultivated with *A. tumefaciens* over a temperature range of at least 18° C. to 28° C. (Table 8). However, there was an indication that at the highest temperature tested, efficiency decline (9% mean) relative to the lower temperatures (32% to 47% means).

TABLE 8

Effect of temperature during co-cultivating *Agrobacterium tumefaciens* and fruit body tissue on the transformation of *Agaricus bisporus*

| Temperature (° C.) | Transformation Efficiency[a] | | | | |
|---|---|---|---|---|---|
| | Exp. I | Exp. II | Exp. III | Exp. IV | Mean |
| 18 | — | — | — | 22/50 (44%) | 44% |
| 20 | 21/50 (42%) | 8/50 (16%) | 37/50 (74%) | 28/50 (56%) | 47% |
| 22 | 15/50 (30%) | 6/50 (12%) | 34/50 (68%) | 14/50 (28%) | 35% |
| 24 | 5/50 (10%) | 9/50 (18%) | 32/50 (64%) | 18/50 (36%) | 32% |
| 26 | 4/50 (8%) | 5/50 (10%) | 38/50 (76%) | 19/50 (38%) | 33% |
| 28 | 5/50 (10%) | 4/50 (8%) | 5/50 (10%) | — | 9% |

[a]Expressed as the number of hygromycin-resistant colonies obtained/number of fruit body tissue pieces plated on selection medium containing 30 µg/ml hygromycin Co-cultivating *A. tumefaciens* and *A. bisporus* fruit body tissue for 1 to 4 days resulted in transformation efficiencies with means for three experiments ranging from 0% to 62% (Table 9). There was a general trend for efficiency to increase with an increase in the duration of co-cultivation.

TABLE 9

Effect of duration of co-cultivating *Agrobacterium tumefaciens* and fruit body tissue on the transformation of *Agaricus bisporus*

| Time (days) | Co-Cultivation Temperature (° C.) | Transformation Efficiency[a] | | | |
|---|---|---|---|---|---|
| | | Exp. I | Exp. II | Exp. III | Mean |
| 1 | 21 | — | — | 0/50 (0%) | 0% |
| | 24 | 4/50 (8%) | 1/50 (2%) | 1/50 (2%) | 4% |
| 2 | 21 | — | — | 10/50 (20%) | 20% |
| | 24 | 20/50 (40%) | 15/50 (30%) | 20/50 (40%) | 37% |
| 3 | 21 | — | — | 29/50 (58%) | 58% |
| | 24 | 21/50 (42%) | 19/50 (38%) | 21/50 (42%) | 41% |
| 4 | 21 | — | — | 31/50 (62%) | 62% |
| | 24 | — | — | 24/50 (48%) | 48% |

Figure 4:
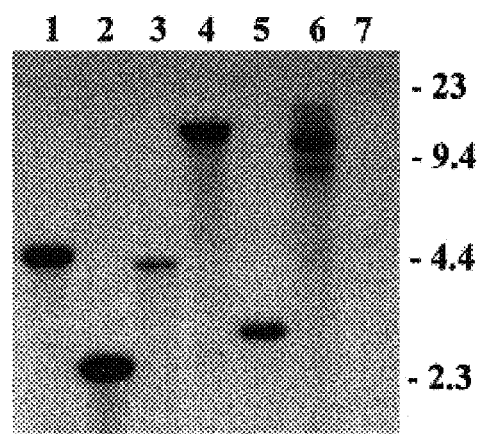
FIG. 4 illustrates Southern blot analysis of DNA isolated from putative hygromycin resistant transformants of *Agaricus bisporus*. Genomic DNA (5–10 μg) was isolated from both cultures, digested with SacI, and probed with an ~1 kb $^{32}$P-labeled HPH gene sequence. Lanes 1–6, DNA isolated from putative transformants AT1-AT6, respectively; Lane 7, DNA isolated from non-transformed *A. bisporus*. The positions of the DNA markers (kb) are shown.
Figure 5:
FIG. 5 shows PCR analysis of DNA isolated from putative hygromycin resistant transformants of *Agaricus bisporus*. PCR amplification was carried out on genomic DNA using primers (gpd-FH/hyg-R) defining an ~970 bp sequence spanning the *A. bisporus* GPD promoter and the HPH gene. Lanes 1–10, DNA isolated from putative transformants AT3, AT4, AT9, AT10, AT11, AT12, AT16, AT19, AT24, and AT31, respectively; Lane 11, negative control with water; Lane 12, DNA isolated from non-transformed *A. bisporus*; Lane 13, positive control with plasmid vector pBGgHg; Lane M, DNA markers (kb).

[a]Expressed as the number of hygromycin-resistant colonies obtained/number of fruit body tissue pieces plated on selection medium containing 30 µg/ml hygromycin Southern blot analyses confirmed that the HPH gene was integrated into the genome of *A. bisporus* (FIG. 4). We detected no false positives by Southern blot analysis or PCR amplification (FIG. 5) among 37 antibiotic resistant cultures.

Figure 6:
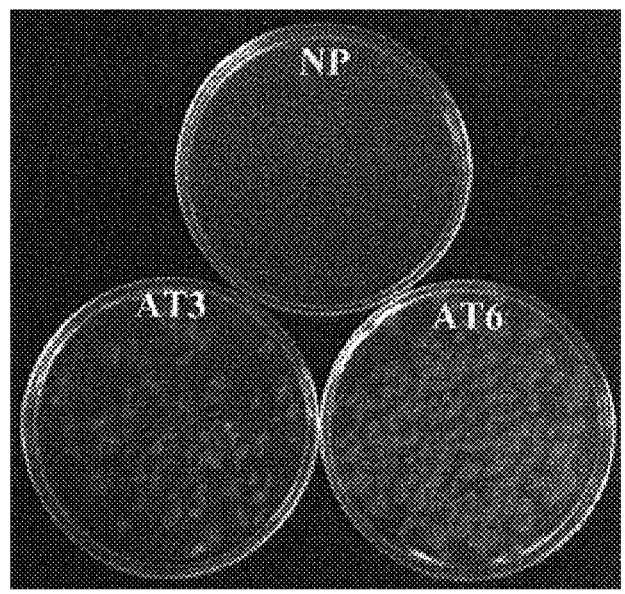
FIG. 6 shows expression of the hygromycin resistance trait in the first-generation basidiospores produced from transgenic cultures of *Agaricus bisporus*. Basidiospores from two transgenic lines (AT3 and AT6) and the non-transformed parental strain (NP) were plated on selection medium with 50 μg/ml of hygromycin. The viability of the basidiospores of the parental strain was established on selection medium without antibiotic (not shown).

The fungal transformation system disclosed herein provides a level of efficiency and utility that is comparable to the 'floral dip' Agro transformation procedure for the model plant system, *Arabidopsis thaliana*. Transgenic vegetative mycelial cultures could be generated in less than 2 weeks, and mature fruit bodies could be produced ~8 weeks later under controlled environmental conditions. Thirty hygromycin-resistant transgenic mushroom lines were cropped and all developed normal fruit bodies. The antibiotic resistance trait was stably maintained in the absence of selection pressure during vegetative growth and reproductive development of the cultures; being expressed by the fruit bodies and basidiospores (FIG. 6).

What is claimed is:

1. A method of transforming *Agaricus bisporus* comprising:

introducing to fruit body tissue cells of said *Agaricus bisporus* a polynucleotide construct desired in said *Agaricus bisporus*, said construct comprising a promoter sequence capable of regulating expression in *Agaricus bisporus* cells, wherein said introducing is by *Agrobacterium*-mediated transformation by co-cultivation of vir induced *Agrobacterium* with *Agaricus* fruit body tissue cells; and thereafter regenerating a transgenic *Agaricus bisporus* from said fruit body tissue cells.

2. The method of claim 1 wherein said fruit body tissue cells comprise a gill tissue.

3. The method of claim 1 wherein said fruit body tissue cells are selected from group consisting of:

gill, cap, stem, veil, and volva.

4. The method of claim 1 wherein said polynucleotide construct comprises an expression cassette.

5. The meihod of claim 1 further comprising the step of regenerating transgenic cultures from said tissue cells.

6. The method of claim 5 wherein said cultures are regenerated in about two weeks.

7. An *Agaricus bisporus* transformation method comprising:

obtaining an *Agrobacterium* vector, said vector comprising a polynucleotide sequence the presence of which is desired in a recipient *Agaricus bisporus* cell, said polynucleotide sequence operatively linked to a promoter sequence capable of regulating expression in *Agaricus bisporus* cells;

introducing said vector to fruit body tissue cells of said *Agaricus bisporus* in the presence of an active vir *Agrobacterium* region and a vir inducing compound by co-cultivation of vir induced *Agrobacterium* with *Agaricus* fruit body tissue cells; and regenerating a transgenic *Agaricus bisporus* from said fruit body cells.

8. The method of claim 7 further comprising the step of regenerating recipient *Agaricus bisporus* cells.

9. The method of claim 7 further comprising the step of selecting transformed cells.

10. The mwthod of claim 7 wherein said polynucleotide sequence comprises an expression construct.

11. The method of claim 10 wherein said expression construct comprises a selectable marker DNA of interest, said selectable marker encoding a polynucleotide sequence operably linked to promoter and termination regions capable of driving expression in an *Agaricus bisporus* cell.

12. The method of claim 10 wherein said expression construct comprises a DNA of interest, said DNA of interest encoding a polynucleotide sequence operably linked to promoter and termination sequences capable of inducing expression in a host cell.

13. The method of claim 7 wherein said vir inducing compound is acetosyringone.

14. A method for transformation of *Agaricus bisporus* fruit body tissue cells comprising:

obtaining an *Agrobacterium* vector, said vector comprising a polynucleotide sequence the presence of which is desired in a recipient *Agaricus bisporus* fruit body tissue cell, said polynucleotide sequence operatively linked to a promoter sequence capable of regulating expression in *Agaricus bisporus* cells and introducing said vector to said *Agaricus bisporus* fruit body tissue cells in the presence of an active vir *Agrobacterium* region and a vir inducing compound by co-cultivation of vir induced *Agrobacterium* with *Agaricus* fruit body tissue cells.

* * * * *

UNITED STATES PATENT AND TRADEMARK OFFICE
CERTIFICATE OF CORRECTION

| | | |
|---|---|---|
| PATENT NO. | : 6,964,866 B2 | Page 1 of 1 |
| APPLICATION NO. | : 09/894630 | |
| DATED | : November 15, 2005 | |
| INVENTOR(S) | : Romaine et al. | |

It is certified that error appears in the above-identified patent and that said Letters Patent is hereby corrected as shown below:

<u>Col. 1, Lines 11-16:</u>
After GRANT REFERENCE, DELETE: "Work for this invention was funded in part by a grant from the United States Department of Agriculture, under the Hatch Act (PEN03568). The Government may have certain rights in this invention."

After GRANT REFERENCE ADD: --This invention was made with government support under Hatch Act Project No. PEN03568, awarded by the United States Department of Agriculture. The Government has certain rights in the invention.--

Signed and Sealed this
Fourteenth Day of June, 2011

David J. Kappos
*Director of the United States Patent and Trademark Office*